(12) United States Patent
Zhou et al.

(10) Patent No.: US 9,291,873 B2
(45) Date of Patent: Mar. 22, 2016

(54) SURFACTANTS WITH A TERMINAL DIALKYL- OR CYCLOALKYL-SUBSTITUTED TERTIARY AMINE AND INKS INCLUDING THE SAME

(75) Inventors: Zhang-Lin Zhou, Palo Alto, CA (US); Qin Liu, Corvallis, OR (US); Mary Elizabeth Parent, Mountain View, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 50 days.

(21) Appl. No.: 14/124,828

(22) PCT Filed: Jun. 10, 2011

(86) PCT No.: PCT/US2011/040050
§ 371 (c)(1),
(2), (4) Date: Dec. 9, 2013

(87) PCT Pub. No.: WO2012/170035
PCT Pub. Date: Dec. 13, 2012

(65) Prior Publication Data
US 2014/0118816 A1    May 1, 2014

(51) Int. Cl.
| | | |
|---|---|---|
| C07D 207/412 | (2006.01) | |
| G02F 1/167 | (2006.01) | |
| C07D 207/40 | (2006.01) | |
| C07D 401/12 | (2006.01) | |
| C07D 403/12 | (2006.01) | |
| C07D 413/12 | (2006.01) | |
| C08G 73/02 | (2006.01) | |
| C09D 11/03 | (2014.01) | |
| C09D 11/10 | (2014.01) | |

(52) U.S. Cl.
CPC ............. *G02F 1/167* (2013.01); *C07D 207/40* (2013.01); *C07D 207/412* (2013.01); *C07D 401/12* (2013.01); *C07D 403/12* (2013.01); *C07D 413/12* (2013.01); *C08G 73/0213* (2013.01); *C09D 11/03* (2013.01); *C09D 11/10* (2013.01)

(58) Field of Classification Search
CPC ................................................... C07D 207/412
See application file for complete search history.

(56) References Cited

U.S. PATENT DOCUMENTS

| | | |
|---|---|---|
| 7,377,974 B2 | 5/2008 | Grimm et al. |
| 7,686,883 B2 | 3/2010 | Kempter et al. |
| 7,938,900 B2 | 5/2011 | Fechner et al. |
| 2004/0029721 A1 | 2/2004 | Wang et al. |
| 2009/0203563 A1 | 8/2009 | Seddon et al. |

FOREIGN PATENT DOCUMENTS

| | | |
|---|---|---|
| DE | 2715886 | 4/1976 |
| JP | 63-254444 | 10/1988 |
| WO | WO-2011046562 | 4/2011 |

OTHER PUBLICATIONS

Wantanabe (CAPLUS Abstract of: Sekiyu Gakkaishi (1971), 14(7), 489-91).*
International Search Report, Feb. 17, 2012, PCT Patent Application No. PCT/US2011/040050, Filed Jun. 10, 2011.

* cited by examiner

*Primary Examiner* — Robert Havlin
(74) *Attorney, Agent, or Firm* — HP Inc. Patent Department

(57) ABSTRACT

Surfactants are provided that have a hydrophobic tail portion and a hydrophilic head portion. The hydrophilic head portion includes a terminal dialkyl-substituted tertiary amine or a terminal cycloalkyl-substituted tertiary amine. Also provided are pigment-based inks employing the surfactant, a combination of an electronic display and the pigment-based inks, and a process for reducing conductivity in primary amine-based surfactants and improving reliability of electronic inks employing such surfactants.

20 Claims, 6 Drawing Sheets

SURFACTANTS WITH A TERMINAL DIALKYL- OR CYCLOALKYL-SUBSTITUTED TERTIARY AMINE AND INKS INCLUDING THE SAME

BACKGROUND

Ultrathin, flexible electronic displays that look like print on paper have many potential applications including wearable computer screens, electronic paper, smart identity cards, store shelf labels, and signage applications. Electrophoretic or electrokinetic displays are an important approach to this type of medium. Electrophoretic actuation relies on particles moving under the influence of an electric field. Accordingly, the desired particles must exhibit good dispersibility and charge properties in non-polar dispersing media. Non-polar dispersing media are desirable because they help minimize the leakage currents in electrophoretic or electrokinetic devices.

Current commercial products based on electrophoretic display technology are only able to provide color and white states or black and white states. They cannot provide a clear or transparent state, which prevents use of a stacked architecture design. A stacked architecture of layered colorants would allow the use of transparent to colored state transitions in each layer of primary subtractive color resulting in print-like color in one display.

BRIEF DESCRIPTION OF THE DRAWINGS

Features and advantages of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Figure 1:
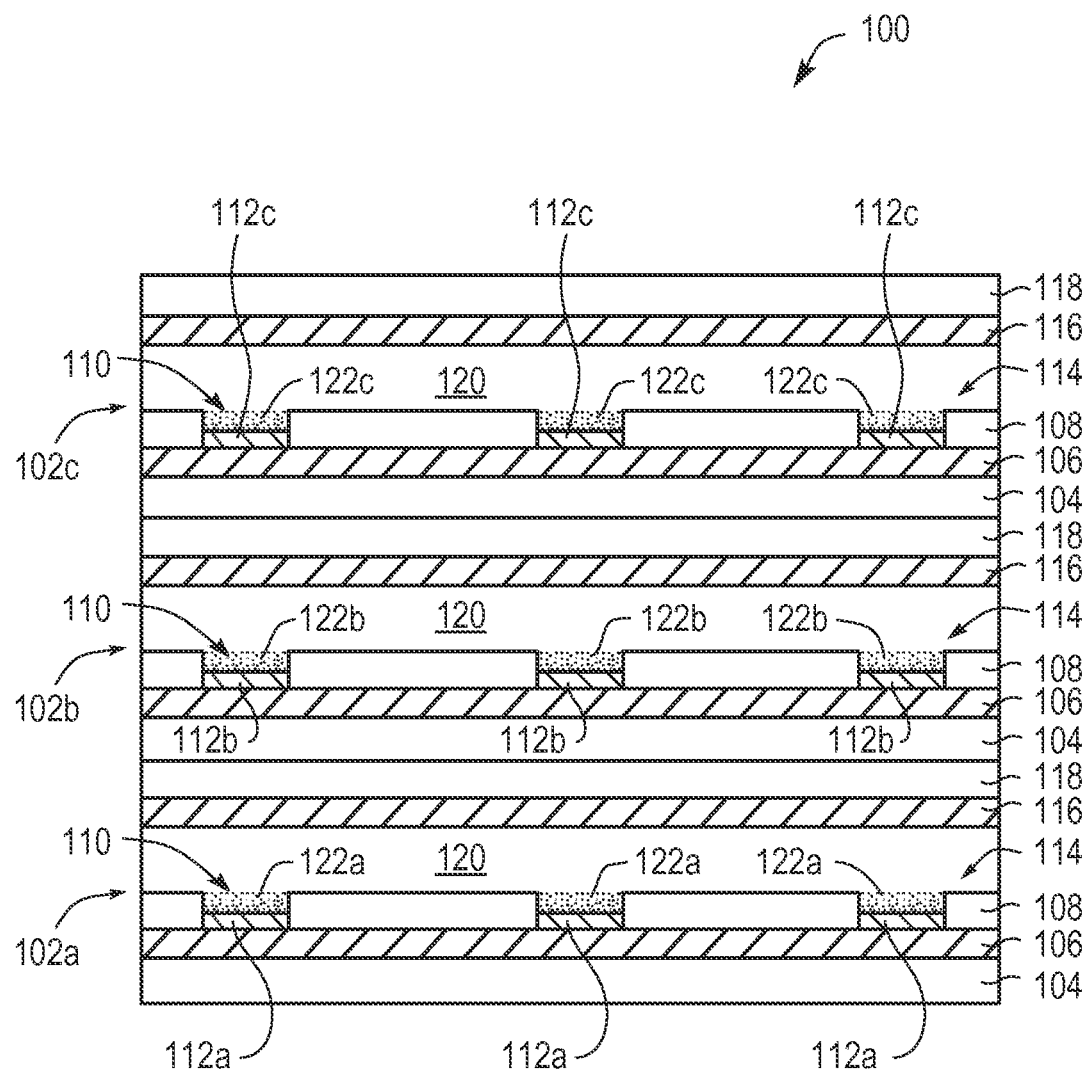
FIG. 1 depicts a cross-sectional view of one example of a stacked electro-optical display.

Reference is made now in detail to specific examples, which illustrate the best mode presently contemplated by the inventors for practicing the invention. Alternative examples are also briefly described as applicable.

In the following detailed description, reference is made to the accompanying drawings which form a part hereof, and in which is shown by way of illustration specific examples in which the disclosure may be practiced. In this regard, directional terminology, such as "top," "bottom," "front," "back," "leading," "trailing," etc., is used with reference to the orientation of the Figure(s) being described. Because components of examples can be positioned in a number of different orientations, the directional terminology is used for purposes of illustration and is in no way limiting. It is to be understood that other examples may be utilized and structural or logical changes may be made without departing from the scope of the present disclosure. The following detailed description, therefore, is not to be taken in a limiting sense, and the scope of the present disclosure is defined by the appended claims.

As used herein, the term "grayscale" applies to both black and white images and monochromatic color images. Grayscale refers to an image including different shades of a single color produced by controlling the density of the single color within a given area of a display.

As used herein, the term "over" is not limited to any particular orientation and can include above, below, next to, adjacent to, and/or on. In addition, the term "over" can encompass intervening components between a first component and a second component where the first component is "over" the second component.

As used herein, the term "adjacent" is not limited to any particular orientation and can include above, below, next to, and/or on. In addition, the term "adjacent" can encompass intervening components between a first component and a second component where the first component is "adjacent" to the second component.

As used herein, the term "electronic ink display" is a display that forms visible images using one or more of electrophoresis, electro-convection, electroosmosis, electrochemical interactions, and/or other electrokinetic phenomena.

As used herein, "about" means a ±10% variance caused by, for example, variations in manufacturing processes.

The article "a" and "an" as used in the claims herein means one or more.

Significant progress has been made towards developing working electronic inks based on the electrokinetic mechanism using conventional stabilization techniques and materials. However, improvements in reliability are still needed for commercially successful applications. These previous electronic inks are based on pigments with additional surfactants and charge directors, in which both charging and stabilization related functionality are not covalently bonded to the pigment surface. In this case, the pigment can lose charge with time under electric field or repeated switching cycles. The adsorbed stabilizing polymer material on the pigment surface is capable of desorbing and the free polymeric species in the solvent are capable of degradation as a result of cell operation. Additional surfactants in the solvent also result in higher background charges can lead to field screening effects.

Stable, charged electrophoretic/electrokinetic pigment suspensions require at least the following three components: (1) pigment, (2) carrier fluid, (3) surfactants. The pigment provides the color and can participate in charging. Key considerations are the particle size, surface functional groups, dispersibility, hue, chroma, and lightness. The carrier fluid acts as a vehicle for dispersing the pigment as well as an electrophoretic medium. When choosing the carrier fluid, its polarity, viscosity, resistivity, specific gravity, chemical stability, and toxicity must all be considered. Examples of carrier fluids include hydrocarbons, halogenated or partially halogenated hydrocarbons, oxygenated fluids, and silicones. The surfactant participates in particle charging, and it can be present directly on the pigment particle surface or on a resin particle that contains pigment. The surfactant also charges the particles, carries counter charges, and helps prevent particle aggregation. It should be colorless and dispersible or soluble in the carrier fluid.

Many small molecules or polymers that can form reverse micelles in non-polar solvents can be used as surfactants for electronic inks. The examples include, but are not limited to, neutral and non-dissociable charge directors such as polyisobutylene succinimide amines 1, ionizable charge directors that can disassociate to form charges such as sodium di-2-ethylhexylsulfosuccinate or dioctyl sulfosuccinate (AOT) 2, zwitterionic charge directors such as Lecithin 3, and non-chargeable and neutral charge directors, which cannot disassociate or react with acid or base to form charges such as fluorosurfactants 4. These specific charge directors are shown in Scheme 1.

Scheme 1

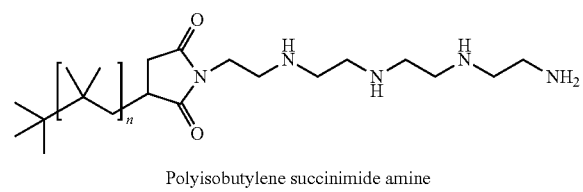

Polyisobutylene succinimide amine

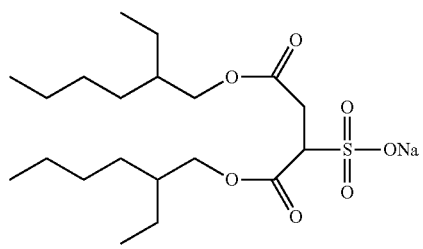

AOT, sodium di-2-ethylhexylsulfosuccinate
Dioctyl sulfosuccinate,

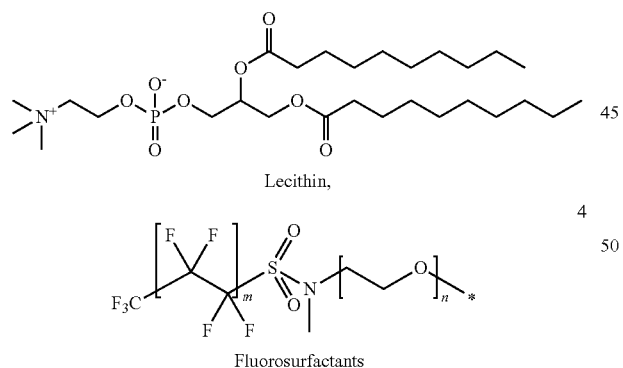

Lecithin,

Fluorosurfactants

Some electronic inks based on the above surfactants have shown reasonable switching performances; however, the reliability of these electronic inks has not met the requirements for commercial applications. Unexpectedly, a new series of surfactants has been discovered, based on dialkyl- or cycloalkyl-substituted tertiary amines. Electronic inks based on these new surfactants have improved reliability.

Figure 2:
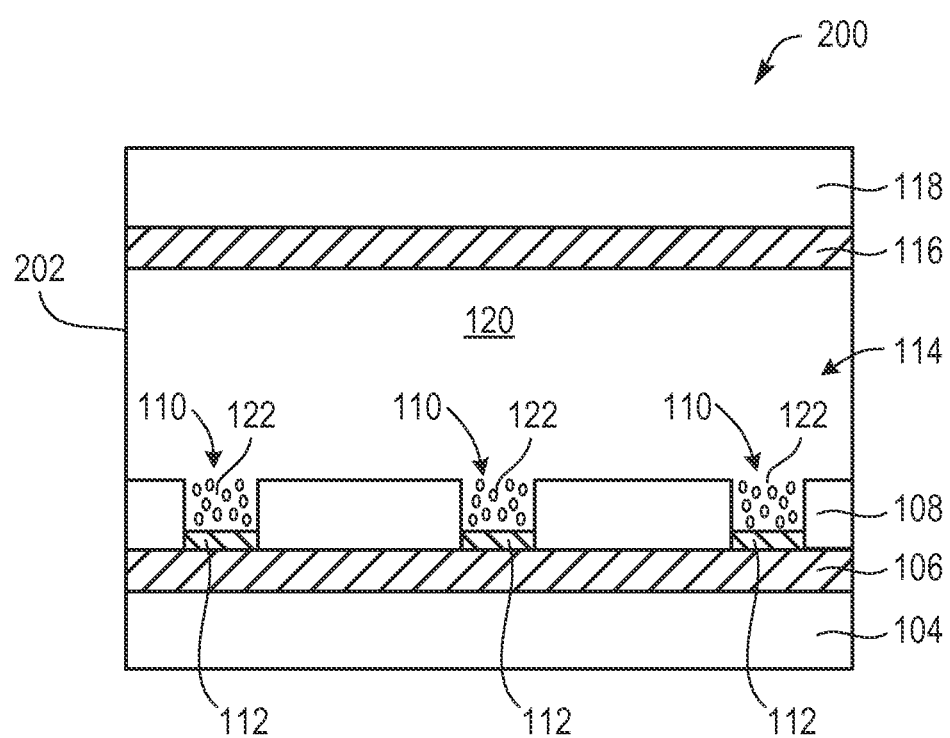
FIG. 2 illustrates a cross-sectional view of one example of a lateral electro-optical display.

Scheme 2 describes a general structure of such surfactants based on dialkyl-substituted and cycloalkyl-substituted polyaliphatic amines I and II, respectively. These surfactants, like many surfactants, have a hydrophobic tail and a hydrophilic head. In particular, these surfactants have polyisobutylene chains as the hydrophobic tail and the dialkyl- or cycloalkyl-substituted polyaliphatic amines as the hydrophilic head. The unique structure feature with a tertiary amine in the end of the hydrophilic head results in lower electrical conductivity. Electronic inks based on such new surfactants have improved reliability. By "improved reliability" is meant an improvement in the ability of the color of the ink to be switched on and off in a reflective display, such as shown in FIGS. 1 and 2.

Scheme 2

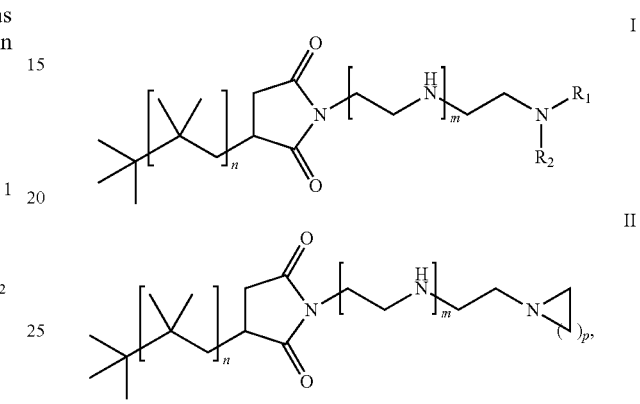

wherein
the letters $R_1$ to $R_2$ each independently represent an optionally substituted alkyl, alkenyl, aryl or aralkyl groups;
the letter m can be any integer from 0 to 6;
the letter n can be any integer from 5 to 500; and
the letter p can be any integer from 1 to 6.

Schemes 3 and 4 describe general examples of such surfactants based on dialkyl- and cycloalkyl-substituted polyaliphatic amines, respectively.

Scheme 3

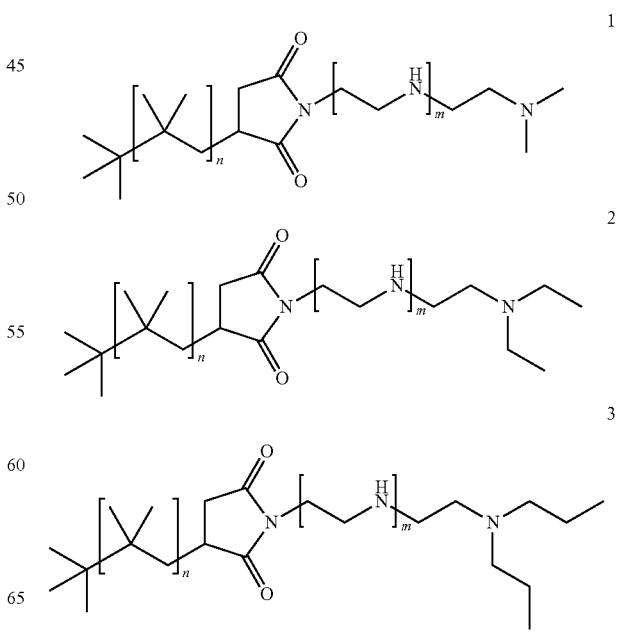

-continued

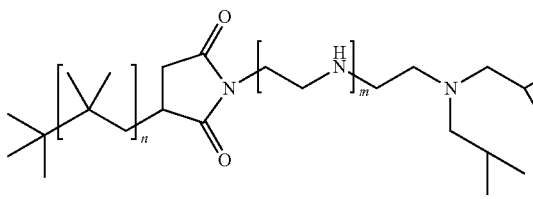

wherein
the letter m can be any integer from 0 to 6; and
the letter n can be any integer from 5 to 500.

Scheme 4

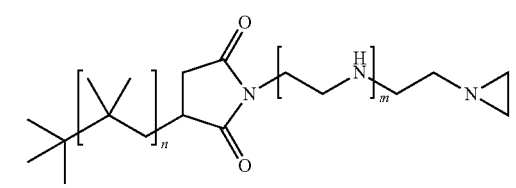

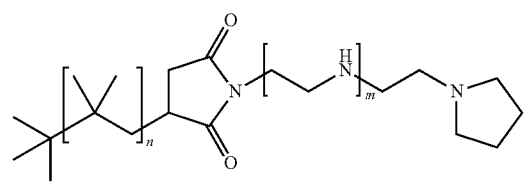

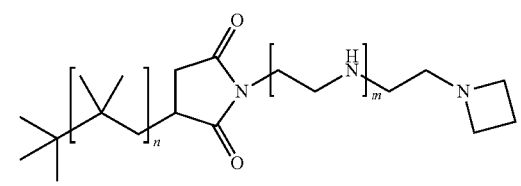

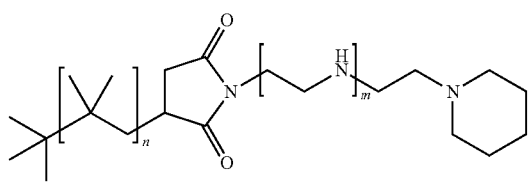

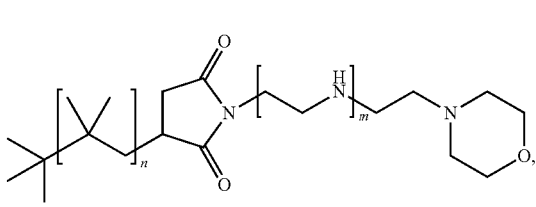

wherein
the letter m can be any integer, from 0 to 6; and
the letter n can be any integer from 5 to 500.

Scheme 5 describes general structures of such surfactants based on dialkyl and cycloalkyl tertiary amine-terminated polyethylene glycols III and IV, respectively. These surfactants have polyisobutylene chains as the hydrophobic tail and dialkyl or cycloalkyl tertiary amine-terminated polyethylene glycols as the hydrophilic head. The unique structure feature with a tertiary amine in the end of the hydrophilic head results in lower conductivity. Electronic inks based such new surfactants have improved reliability.

Scheme 5

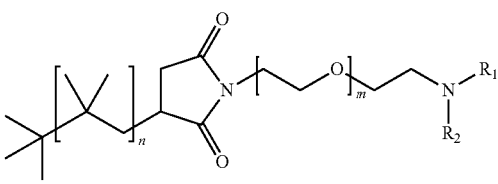

III

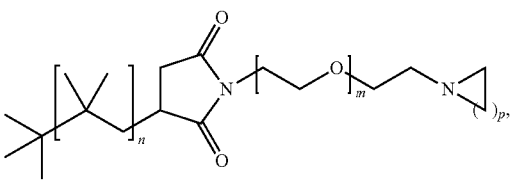

IV wherein
the letters $R_1$ to $R_2$ each independently represent a substituted alkyl, alkenyl, aryl or aralkyl groups;
the letter m can be any integer from 0 to 6;
the letter n can be any integer number, from 5 to 500; and
the letter p can be any integer number, from 1 to 6.

Schemes 6 and 7 describe general examples of such surfactants based on dialkyl and cycloalkyl tertiary amine-terminated polyethylene glycols, respectively.

Scheme 6

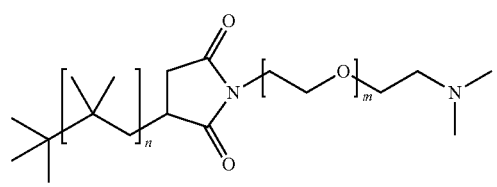

10

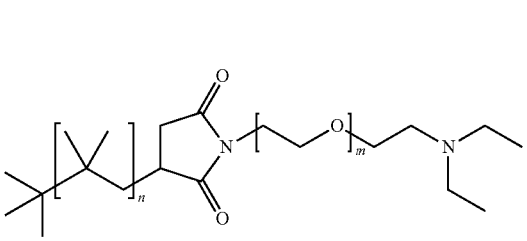

11

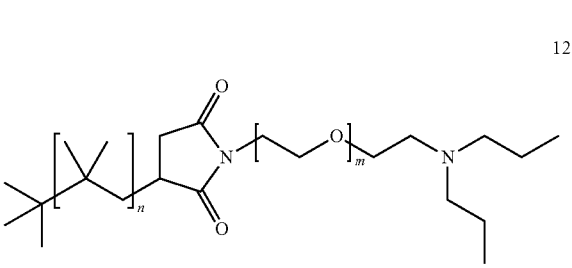

12

-continued

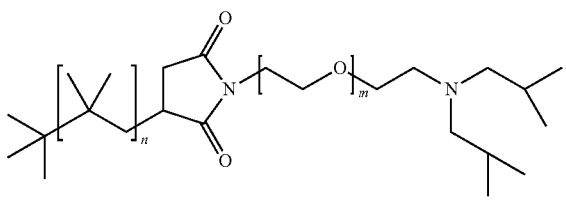

13 wherein
the letter m can be any integer from 0 to 6; and
the letter n can be any integer from 5 to 500.

Scheme 7

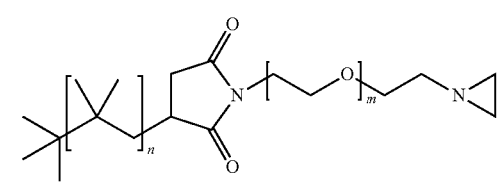

14

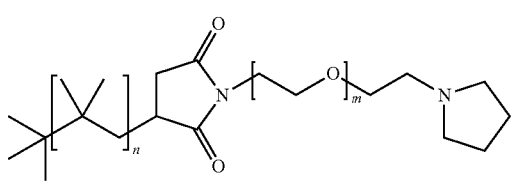

15

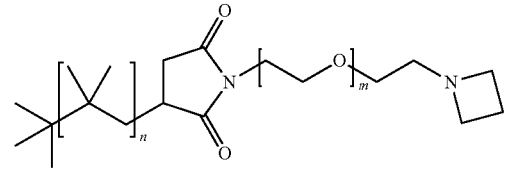

16

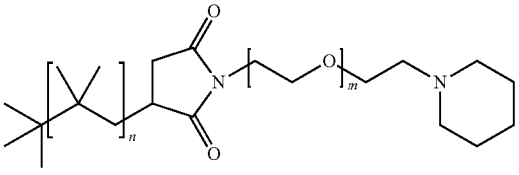

17

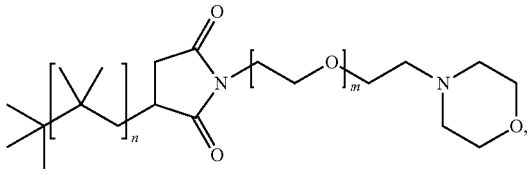

18 wherein
the letter m can be any integer from 0 to 6; and
the letter n can be any integer from 5 to 500.

Scheme 8 describes general structures of such surfactants based on dialkyl and cycloalkyl tertiary amine-terminated alkanes V and VI, respectively. These surfactants have polyisobutylene chains as the hydrophobic tail and dialkyl or cycloalkyl tertiary amine-terminated alkanes as the hydrophilic head. The unique structure feature with a tertiary amine in the end of the hydrophilic head results in lower conductivity. Electronic inks based on such new surfactants have improved reliability.

Scheme 8

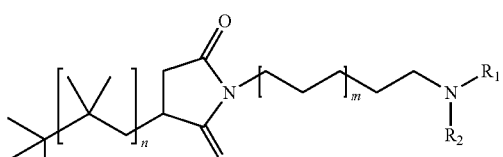

V

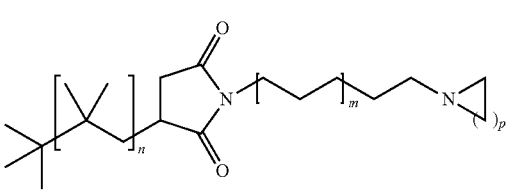

VI wherein
the letters $R_1$ to $R_2$ each independently represent a substituted alkyl, alkenyl, aryl or aralkyl groups;
the letter m can be any integer from 0 to 6;
the letter n can be any integer from 5 to 500; and
the letter p can be any integer from 1 to 6.

Schemes 9 and 10 describe general examples of such surfactants based on dialkyl and cycloalkyl tertiary amine-terminated alkanes, respectively.

Scheme 9

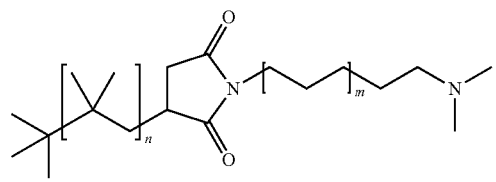

19

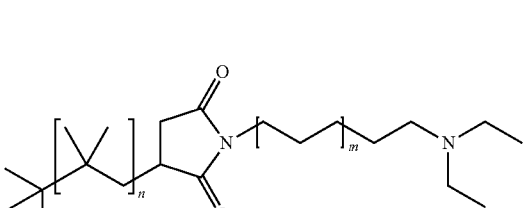

20

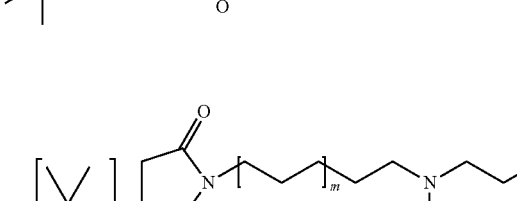

21

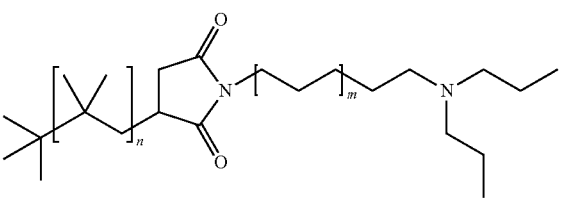

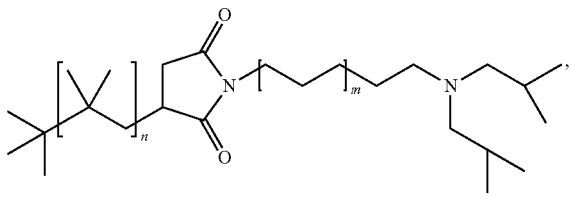

wherein
the letter m can be any integer from 0 to 6; and
the letter n can be any integer from 5 to 500.

Scheme 10

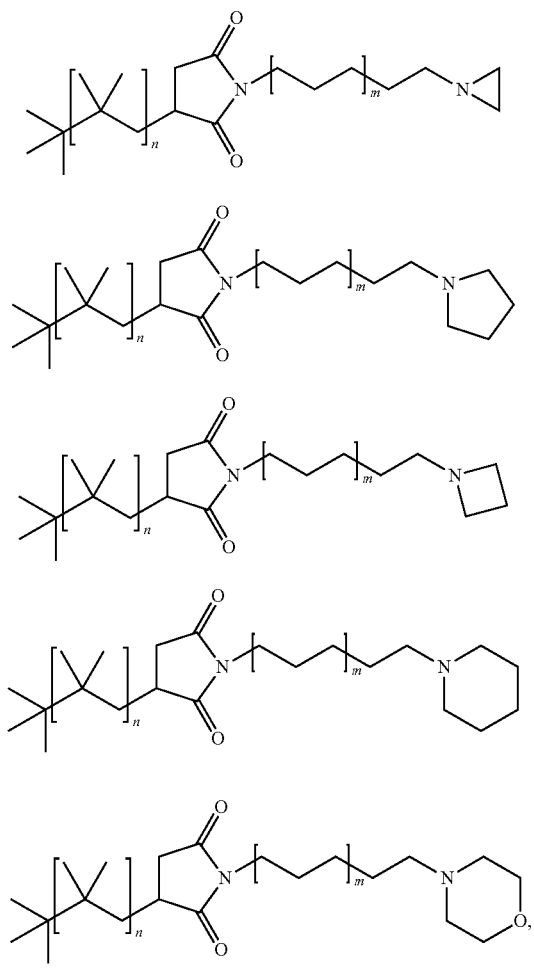

wherein
the letter m can be any integer from 0 to 6; and
the letter n can be any integer from 5 to 500.

Turning now to electronic inks that employ the surfactants discussed above, examples of such electronic inks generally include a non-polar carrier fluid (i.e., a fluid having a low dielectric constant k such as, e.g., less than about 20, or, in some cases, less than about 2) and a pigment. Such carrier fluids tend to reduce leakages of electric current when driving the display, as well as increase the electric field present in the fluid. As used herein, the "carrier fluid" is a fluid or medium that fills up a viewing area defined in an electronic ink display and is generally configured as a vehicle to carry colorant particles therein. In response to a sufficient electric potential or field applied to the colorant particles while driving electrodes of the display, the colorant particles tend to move and/or rotate to various spots within the viewing area in order to produce a desired visible effect in the display cell to display an image. The non-polar carrier fluid includes, for example, one or more non-polar carrier fluids selected from hydrocarbons, halogenated or partially halogenated hydrocarbons, and/or siloxanes. Some specific examples of non-polar carrier fluids include perchloroethylene, cyclohexane, dodecane, mineral oil, isoparaffinic fluids, cyclopentasiloxane, cyclohexasiloxane, octamethylcyclosiloxane, and combinations thereof.

The surfactant may be dispersed in the carrier fluid. The concentration of the surfactant in the electronic ink may be in the range of about 0.05 to 20 percent by weight (wt %) in some examples. In other examples, the concentration of the surfactant in the electronic ink may be in the range of about 0.1 to 10 wt %. The surfactants disclosed herein may partially or even totally replace other components often used in electronic inks, such as dispersants and/or charge directors.

The colorant particles are dispersed in the carrier fluid. As used herein, the term "colorant particles" refers to particles that produce a color. Some non-limiting examples of suitable colorant particles include surface-modified pigment particles. In a non-limiting example, the colorant particles may be selected from pigment particles that are self-dispersible in the non-polar carrier fluid. It is to be understood, however, that non-dispersible pigment particles may otherwise be used so long as the electronic ink includes one or more suitable dispersants. Such dispersants include hyperdispersants such as those of the SOLSPERSE® series manufactured by Lubrizol Corp., Wickliffe, Ohio (e.g., SOLSPERSE® 3000, SOLSPERSE® 8000, SOLSPERSE® 9000, SOLSPERSE® 11200, SOLSPERSE® 13840, SOLSPERSE® 16000, SOLSPERSE® 17000, SOLSPERSE® 18000, SOLSPERSE® 19000, SOLSPERSE® 21000, and SOLSPERSE® 27000); various dispersants manufactured by BYK-chemie, Gmbh, Germany, (e.g., DISPERBYK® 110, DISPERBYK® 163, DISPERBYK® 170, and DISPERBYK® 180); various dispersants manufactured by Evonik Goldschmidt GMBH LLC, Germany, (e.g., TEGO® 630, TEGO® 650, TEGO® 651, TEGO® 655, TEGO® 685, and TEGO® 1000); and various dispersants manufactured by Sigma-Aldrich, St. Louis, Mo., (e.g., SPAN® 20, SPAN® 60, SPAN® 80, and SPAN® 85).

In some examples, the concentration of pigment in the electronic ink ranges from about 0.5 to 20 percent by weight (wt %). In other examples, the concentration of the pigment ranges from about 1 to 10 wt %. In some examples, the concentration of dispersant in the electronic ink ranges from about 0.5 to 20 percent by weight (wt %). In other examples, the concentration of the dispersant ranges from about 1 to 10 wt %. The carrier fluid makes up the balance of the ink.

There is commonly a charge director employed in electronic inks. As used herein, the term "charge director" refers to a material that, when used, facilitates charging of the colorant particles. In an example, the charge director is basic and reacts with the acid-modified colorant particle to negatively charge the particle. In other words, the charging of the particle is accomplished via an acid-base reaction between the charge director and the acid-modified particle surface. It is to be understood that the charge director may also be used in the electronic ink to prevent undesirable aggregation of the colorant in the carrier fluid. In other cases, the charge director is acidic and reacts with the base-modified colorant particle to positively charge the particle. Again, the charging of the particle is accomplished via an acid-base reaction between the charge director and the base-modified particle surface or adsorption of charged micelles.

The charge director may be selected from small molecules or polymers that are capable of forming reverse micelles in the non-polar carrier fluid. Such charge directors are generally colorless and tend to be dispersible or soluble in the carrier fluid.

In a non-limiting example, the charge director is selected from a neutral and non-dissociable monomer or polymer such as, e.g., a polyisobutylene succinimide amine, which has a molecular structure as follows:

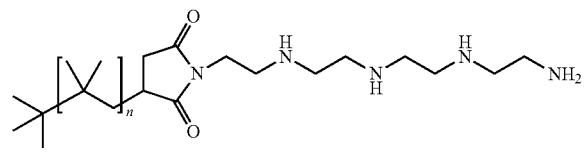

where n is selected from a whole number ranging from 15 to 100.

Another example of the charge director includes an ionizable molecule that is capable of disassociating to form charges. Non-limiting examples of such charge directors include sodium di-2-ethylhexylsulfosuccinate and dioctyl sulfosuccinate. The molecular structure of dioctyl sulfosuccinate is as follows:

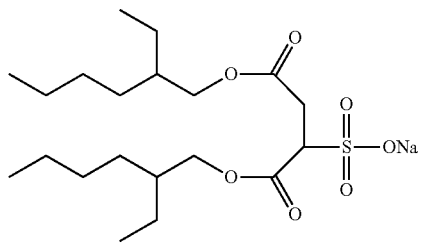

Yet another example of the charge director includes a zwitterion charge director such as, e.g., lecithin. The molecular structure of lecithin is as shown as follows:

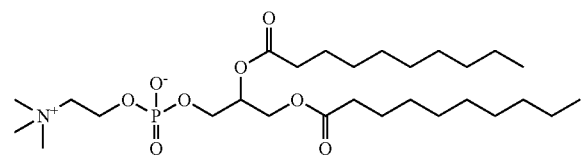 [SMILES: CCCCCCCCCC(=O)OCC(COP(=O)([O-])OCC[N+](C)(C)C)OC(=O)CCCCCCCCC]

The pigment particles are selected from organic or inorganic pigments, and have an average particle size ranging from about 1 nm to about 10 μm. In some examples, the average particle size ranges from about 10 nm to about 1 μm. In other examples, the average particle size ranges from about 30 to 500 nm. In still other examples, the average particle size ranges from about 50 nm to 1 μm. Such organic or inorganic pigment particles may be selected from black pigment particles, yellow pigment particles, magenta pigment particles, red pigment particles, violet pigments, cyan pigment particles, blue pigment particles, green pigment particles, orange pigment particles, brown pigment particles, and white pigment particles. In some instances, the organic or inorganic pigment particles may include spot-color pigment particles, which are formed from a combination of a predefined ratio of two or more primary color pigment particles.

A non-limiting example of a suitable inorganic black pigment includes carbon black. Examples of carbon black pigments include those manufactured by Mitsubishi Chemical Corporation, Japan (such as, e.g., carbon black No. 2300, No. 900, MCF88, No. 33, No. 40, No. 45, No. 52, MA7, MA8, MA100, and No. 2200B); various carbon black pigments of the RAVEN® series manufactured by Columbian Chemicals Company, Marietta, Ga., (such as, e.g., RAVEN® 5750, RAVEN® 5250, RAVEN® 5000, RAVEN® 3500, RAVEN® 1255, and RAVEN® 700); various carbon black pigments of the REGAL® series, the MOGUL® series, or the MONARCH® series manufactured by Cabot Corporation, Boston, Mass., (such as, e.g., REGAL® 400R, REGAL® 330R, REGAL® 660R, MOGUL® L, MONARCH® 700, MONARCH® 800, MONARCH® 880, MONARCH® 900, MONARCH® 1000, MONARCH® 1100, MONARCH® 1300, and MONARCH® 1400); and various black pigments manufactured by Evonik Degussa Corporation, Parsippany, N.J., (such as, e.g., Color Black FW1, Color Black FW2, Color Black FW2V, Color Black FW18, Color Black FW200, Color Black S150, Color Black S160, Color Black S170, PRINTEX® 35, PRINTEX® U, PRINTEX® V, PRINTEX® 140U, Special Black 5, Special Black 4A, and Special Black 4). A non-limiting example of an organic black pigment includes aniline black, such as C.I. Pigment Black 1.

Other examples of inorganic pigments include metal oxides and ceramics, such as the oxides of titanium, iron, zinc, cobalt, manganese, and nickel. Non-limiting examples of suitable inorganic pigments include those from the Shephord Color Company (Cincinnati, Ohio) such as Black 10C909A, Black 10P922, Black 1G, Black 20F944, Black 30C933, Black 30C940, Black 30C965, Black 376A, Black 40P925, Black 411A, Black 430, Black 444, Blue 10F545, Blue 10G511, Blue 10G551, Blue 10K525, Blue 10K579, Blue 211, Blue 212, Blue 214, Blue 300527, Blue 300588, Blue 300591, Blue 385, Blue 40P585, Blue 424, Brown 100873, Brown 10P835, Brown 10P850, Brown 10P857, Brown 157, Brown 20C819, Green 10K637, Green 187 B, Green 223, Green 260, Green 300612, Green 300654, Green 300678, Green 40P601, Green 410, Orange 10P320, StarLight FL 37, StarLight FL105, StarLight FL500, Violet 11, Violet 11C, Violet 92, Yellow 100112, Yellow 100242, Yellow 100272, Yellow 10P110, Yellow 10P225, Yellow 10P270, Yellow 196, Yellow 20P296, Yellow 300119, Yellow 300236, Yellow 40P140, Yellow 40P280.

The following are examples of organic pigments that may be used in the practice of the various examples disclosed herein.

Non-limiting examples of suitable yellow pigments include C.I. Pigment Yellow 1, C.I. Pigment Yellow 2, C.I. Pigment Yellow 3, C.I. Pigment Yellow 4, C.I. Pigment Yellow 5, C.I. Pigment Yellow 6, C.I. Pigment Yellow 7, C.I. Pigment Yellow 10, C.I. Pigment Yellow 11, C.I. Pigment Yellow 12, C.I. Pigment Yellow 13, C.I. Pigment Yellow 14, C.I. Pigment Yellow 16, C.I. Pigment Yellow 17, C.I. Pigment Yellow 24, C.I. Pigment Yellow 34, C.I. Pigment Yellow 35, C.I. Pigment Yellow 37, C.I. Pigment Yellow 53, C.I. Pigment Yellow 55, C.I. Pigment Yellow 65, C.I. Pigment Yellow 73, C.I. Pigment Yellow 74, C.I. Pigment Yellow 75, C.I. Pigment Yellow 81, C.I. Pigment Yellow 83, C.I. Pigment Yellow 93, C.I. Pigment Yellow 94, C.I. Pigment Yellow 95, C.I. Pigment Yellow 97, C.I. Pigment Yellow 98, C.I. Pigment Yellow 99, C.I. Pigment Yellow 108, C.I. Pigment Yellow 109, C.I. Pigment Yellow 110, C.I. Pigment Yellow 113, C.I. Pigment Yellow 114, C.I. Pigment Yellow 117, C.I. Pigment Yellow 120, C.I. Pigment Yellow 124, C.I. Pigment Yellow 128, C.I. Pigment Yellow 129, C.I. Pigment Yellow 133, C.I. Pigment Yellow 138, C.I. Pigment Yellow 139, C.I. Pigment Yellow 147, C.I. Pigment Yellow 151, C.I. Pigment Yellow 153, C.I. Pigment Yellow 154, Pigment Yellow 155, C.I. Pigment Yellow 167, C.I. Pigment Yellow 172, and C.I. Pigment Yellow 180.

Non-limiting examples of suitable magenta or red or violet organic pigments include C.I. Pigment Red 1, C.I. Pigment Red 2, C.I. Pigment Red 3, C.I. Pigment Red 4, C.I. Pigment Red 5, C.I. Pigment Red 6, C.I. Pigment Red 7, C.I. Pigment Red 8, C.I. Pigment Red 9, C.I. Pigment Red 10, C.I. Pigment Red 11, C.I. Pigment Red 12, C.I. Pigment Red 14, C.I. Pigment Red 15, C.I. Pigment Red 16, C.I. Pigment Red 17, C.I. Pigment Red 18, C.I. Pigment Red 19, C.I. Pigment Red 21, C.I. Pigment Red 22, C.I. Pigment Red 23, C.I. Pigment Red 30, C.I. Pigment Red 31, C.I. Pigment Red 32, C.I. Pigment Red 37, C.I. Pigment Red 38, C.I. Pigment Red 40, C.I. Pigment Red 41, C.I. Pigment Red 42, C.I. Pigment Red 48(Ca), C.I. Pigment Red 48(Mn), C.I. Pigment Red 57(Ca), C.I. Pigment Red 57:1, C.I. Pigment Red 88, C.I. Pigment Red 112, C.I. Pigment Red 114, C.I. Pigment Red 122, C.I. Pigment Red 123, C.I. Pigment Red 144, C.I. Pigment Red 146, C.I. Pigment Red 149, C.I. Pigment Red 150, C.I. Pigment Red 166, C.I. Pigment Red 168, C.I. Pigment Red 170, C.I. Pigment Red 171, C.I. Pigment Red 175, C.I. Pigment Red 176, C.I. Pigment Red 177, C.I. Pigment Red 178, C.I. Pigment Red 179, C.I. Pigment Red 184, C.I. Pigment Red 185, C.I. Pigment Red 187, C.I. Pigment Red 202, C.I. Pigment Red 209, C.I. Pigment Red 219, C.I. Pigment Red 224, C.I. Pigment Red 245, C.I. Pigment Violet 19, C.I. Pigment Violet 23, C.I. Pigment Violet 32, C.I. Pigment Violet 33, C.I. Pigment Violet 36, C.I. Pigment Violet 38, C.I. Pigment Violet 43, and C.I. Pigment Violet 50.

Non-limiting examples of blue or cyan organic pigments include C.I. Pigment Blue 1, C.I. Pigment Blue 2, C.I. Pigment Blue 3, C.I. Pigment Blue 15, C.I. Pigment Blue 15:3, C.I. Pigment Blue 15:34, C.I. Pigment Blue 15:4, C.I. Pigment Blue 16, C.I. Pigment Blue 18, C.I. Pigment Blue 22, C.I. Pigment Blue 25, C.I. Pigment Blue 60, C.I. Pigment Blue 65, C.I. Pigment Blue 66, C.I. Vat Blue 4, and C.I. Vat Blue 60.

Non-limiting examples of green organic pigments include C.I. Pigment Green 1, C.I. Pigment Green 2, C.I. Pigment Green, 4, C.I. Pigment Green 7, C.I. Pigment Green 8, C.I. Pigment Green 10, C.I. Pigment Green 36, and C.I. Pigment Green 45.

Non-limiting examples of brown organic pigments include C.I. Pigment Brown 1, C.I. Pigment Brown 5, C.I. Pigment Brown 22, C.I. Pigment Brown 23, C.I. Pigment Brown 25, and C.I. Pigment Brown, C.I. Pigment Brown 41, and C.I. Pigment Brown 42.

Non-limiting examples of orange organic pigments include C.I. Pigment Orange 1, C.I. Pigment Orange 2, C.I. Pigment Orange 5, C.I. Pigment Orange 7, C.I. Pigment Orange 13, C.I. Pigment Orange 15, C.I. Pigment Orange 16, C.I. Pigment Orange 17, C.I. Pigment Orange 19, C.I. Pigment Orange 24, C.I. Pigment Orange 34, C.I. Pigment Orange 36, C.I. Pigment Orange 38, C.I. Pigment Orange 40, C.I. Pigment Orange 43, and C.I. Pigment Orange 66.

The foregoing surfactants have been described with specific application to electronic inks. However, the surfactants may find use in other ink technologies that employ non-aqueous inks. An example of such other ink technology is liquid electrophotography ink (LEP) used in commercial digital printers.

EXAMPLES

Example 1

General Synthesis of Dialkyl or Cycloalkyl Substituted Polyaliphatic Amines I and II A mixture of polyisobutylene succinic anhydride (5 g, 5 mmol), dialkyl or cycloalkyl substituted polyaliphatic amine (5 mmol) in 60 mL of xylene is refluxed for 8 hours. After cooling down to room temperature, the solution is washed with 0.5 M $NaHCO_3$ (3 times, 10 ml each time), 0.5 M HCl (3 times, 10 ml each time), deionized-$H_2O$ (3 times, 10 ml each time). The organic layer is dried under $MgSO_4$ and the solvent is dried by rotary evaporator, yielding a brownish viscous liquid. The liquid is further purified by column chromatography, eluting with hexane/ethyl acetate (10:1), then eluting with THF (tetrahydrofuran), then eluting with $CHCl_3$/MeOH (methyl alcohol) (98:2), affording the final pure product.

Example 2

General Synthesis of Dialkyl or Cycloalkyl Tertiary Amines Terminated Polyethylene Glycols III and IV A mixture of polyisobutylene succinic anhydride (5 g, 5 mmol), dialkyl or cycloalkyl substituted tertiary amines terminated polyethylene glycols (5 mmol) in 60 mL of xylene is refluxed for 8 hours. After cooling down to room temperature, the solution is washed with 0.5 M $NaHCO_3$ (3 times, 10 ml each time), 0.5 M HCl (3 times, 10 ml each time), deionized-$H_2O$ (3 times, 10 ml each time). The organic layer is dried under $MgSO_4$ and the solvent is dried by rotary evaporator, yielding a brownish viscous liquid. The liquid is further purified by column chromatography, eluting with hexane/ethyl acetate (10:1), then eluting with THF, then eluting with $CHCl_3$/MeOH (98:2), affording the final pure product.

Example 3

General Synthesis of Dialkyl or Cycloalkyl Tertiary Amines Terminated Alkanes V and VI A mixture of polyisobutylene succinic anhydride (5 g, 5 mmol), dialkyl or cycloalkyl tertiary amines terminated alkanes (5 mmol) in 60 mL of xylene is refluxed for 8 hours. After cooling down to room temperature, the solution is washed with 0.5 M $NaHCO_3$ (3 times, 10 ml each time), 0.5 M HCl (3 times, 10 ml each time), deionized-$H_2O$ (3 times, 10 ml each time). The organic layer is dried under $MgSO_4$ and the solvent is dried by rotary evaporator, yielding a brownish viscous liquid. The liquid is further purified by column chromatography, eluting with hexane/ethyl acetate (10:1), then eluting with THF, then eluting with $CHCl_3$/MeOH (98:2), affording the final pure product.

Example 4

Synthesis of Polyaliphatic Amines (HP-PBT)

A mixture of polyisobutylene succinic anhydride (5 g, 5 mmol), diethylenetriamine (0.58 g, 5 mmol) in 60 mL of xylenes was refluxed for 8 hours. After cooling down to room temperature, the solution was washed with 0.5 M NaHCO$_3$ (3 times, 10 ml each time), 0.5 M HCl (3 times, 10 ml each time), DI-H$_2$O (3 times, 10 ml each time). The organic layer was dried under MgSO$_4$ and the solvent was dried by rotary evaporator, yielding a brownish viscous liquid (~60%). The liquid was further purified by column chromatography, eluting with hexane/ethyl acetate (10:1), then eluting with THF, then elute with CHCl$_3$/MeOH (98:2), affording the final pure product, polyisobutylene succinimide diethylenetriamine.

Example 5

Synthesis of Diethyl-Substituted Polyaliphatic Amines (HP-DEPBT)

A mixture of polyisobutylene succinic anhydride (5 g, 5 mmol), N,N-diethyldiethylenetriamine (0.78 g, 5 mmol) in 60 mL of xylenes was refluxed for 8 hours. After cooling down to room temperature, the solution was washed with 0.5 M NaHCO$_3$ (3 times, 10 ml each time), 0.5 M HCl (3 times, 10 ml each time), DI-H$_2$O (3 times, 10 ml each time). The organic layer was dried under MgSO$_4$ and the solvent was dried by rotary evaporator, yielding a brownish viscous liquid (~60%). The liquid was further purified by column chromatography, eluting with hexane/ethyl acetate (10:1), then eluting with THF, then elute with CHCl$_3$/MeOH (98:2), affording the final pure product, polyisobutylene succinimide N,N-diethyldiethylenetriamine.

Example 6

Charge Concentration of Example Surfactant Solutions

Figure 3:
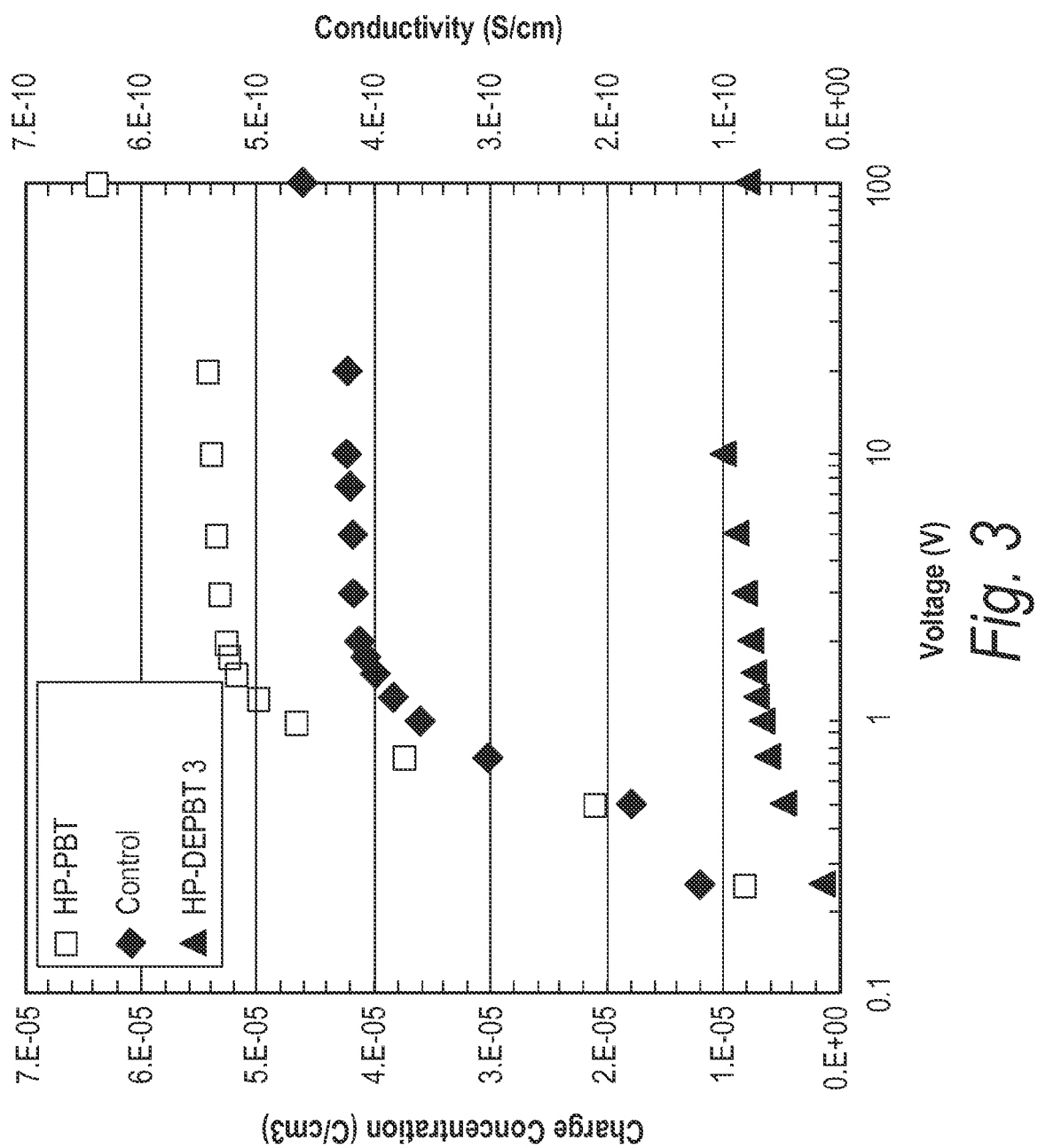
FIG. 3, on coordinates of charge concentration (in $C/cm^3$) (left axis) and conductivity (in S/cm) (right axis) and voltage (in V), shows the charge concentration at various applied voltages and conductivity for three different surfactant solutions, in accordance with an example.

FIG. 3 shows the charge concentration (left axis) and conductivity (right axis), both as a function of applied voltage, for three different surfactant solutions (two example compositions and one control). The nomenclature for the example surfactants and control shown in FIGS. 3-6 is listed in the Table below.

| CODE | CHEMICAL NAME |
| --- | --- |
| HP-PBT | polyisobutylene succinimide diethylenetriamine |
| HP-DEPBT | polyisobutylene succinimide N,N-diethyldiethylenetriamine |
| HP-DIPBT | dipolyisobutylene succinimide diethylenetriamine |
| Control | polyisobutylene succinimide amines |

In FIG. 3, the notation "E-05" means $10^{-5}$. Thus, "2E-05"=$2\times10^{-5}$.

The new surfactant (HP-DEPBT in triangles) shows the lowest charge concentration and the lowest conductivity.

Figure 4:
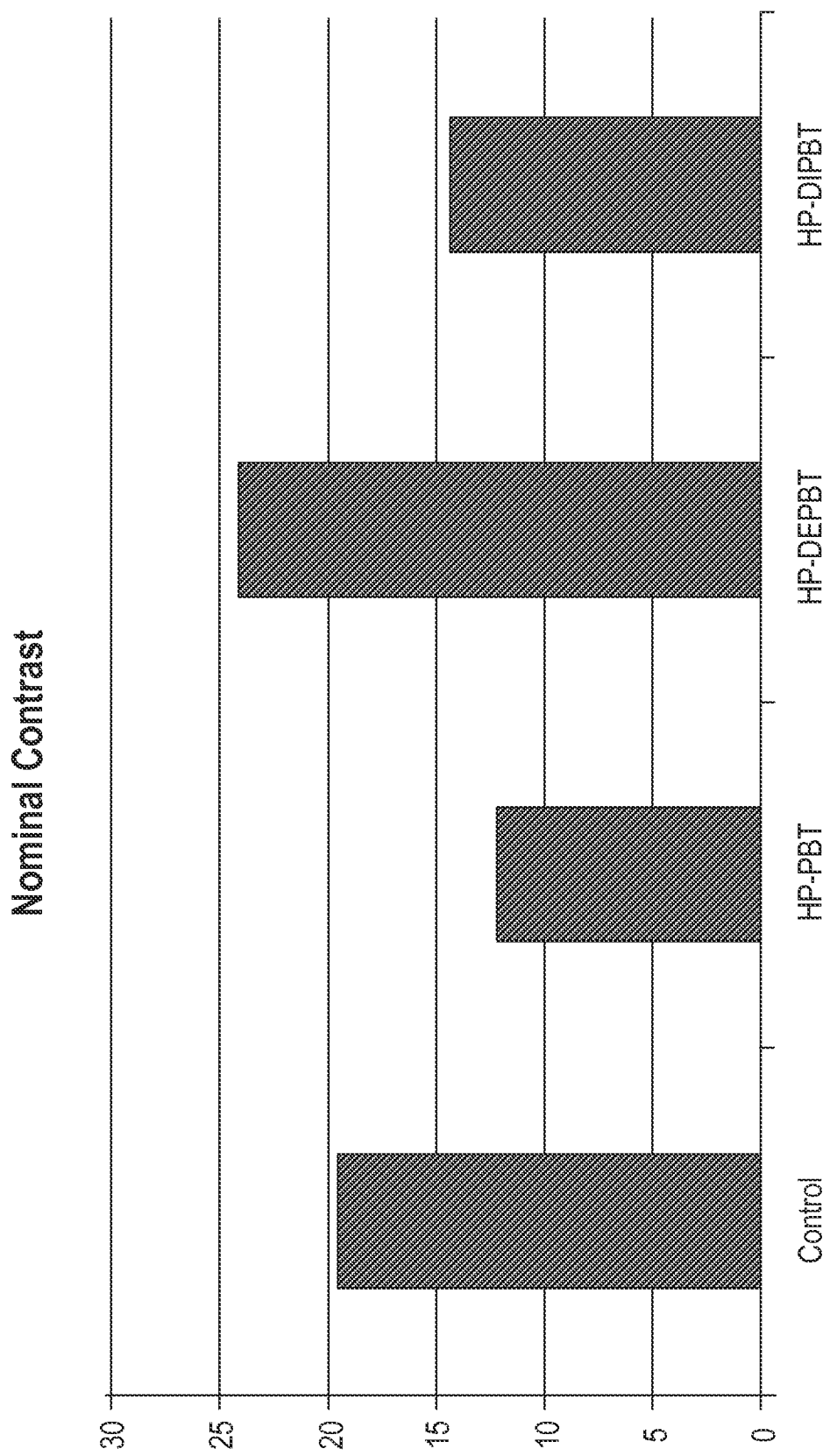
FIG. 4 is a plot showing the initial nominal contrast for devices containing four different surfactant additives, in accordance with an example.

FIG. 4 shows initial nominal contrast for display devices, each containing an electronic ink with one of four different surfactant additives. The electronic inks were placed in the display elements such as shown in FIG. 1. All inks included a pigment, carrier fluid ISOPAR®, and one of the surfactant additives indicated above. ISOPAR® is the brand name for several grades of high-purity isoparaffinic solvents with narrow boiling ranges, available from Exxon Mobile Corporation (Houston, Tex.). The device containing the new surfactant (HP-DEPBT) yielded the highest nominal contrast among the samples.

Figure 5:
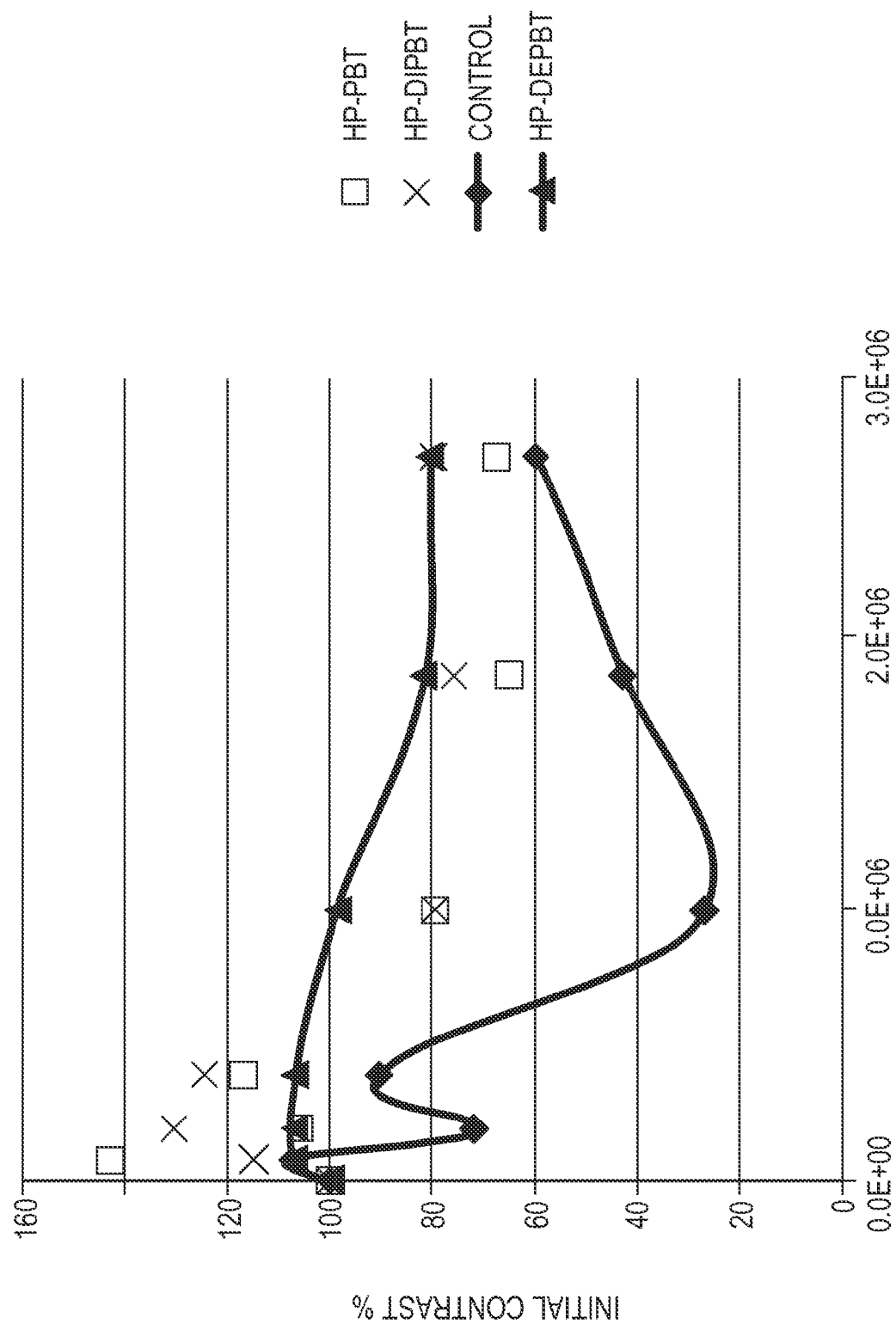
FIG. 5, on coordinates of initial contrast (in %) and normalized test cycles, is a plot of the percent initial contrast as a function of test cycles (normalized), in accordance with an example.

FIG. 5 shows the percent initial contrast vs. normalized test cycles plot. In FIG. 5, the notation "E+06" means $10^6$. Thus, "2.0E+06"=$2\times10^6$. The term "normalized test cycles" refers to the number of times an ink can be cycled through the light and dark states. The device containing the new surfactant (HP-DEPBT) had better initial contrast and retention of the initial contrast than the control and other additives.

Figure 6:
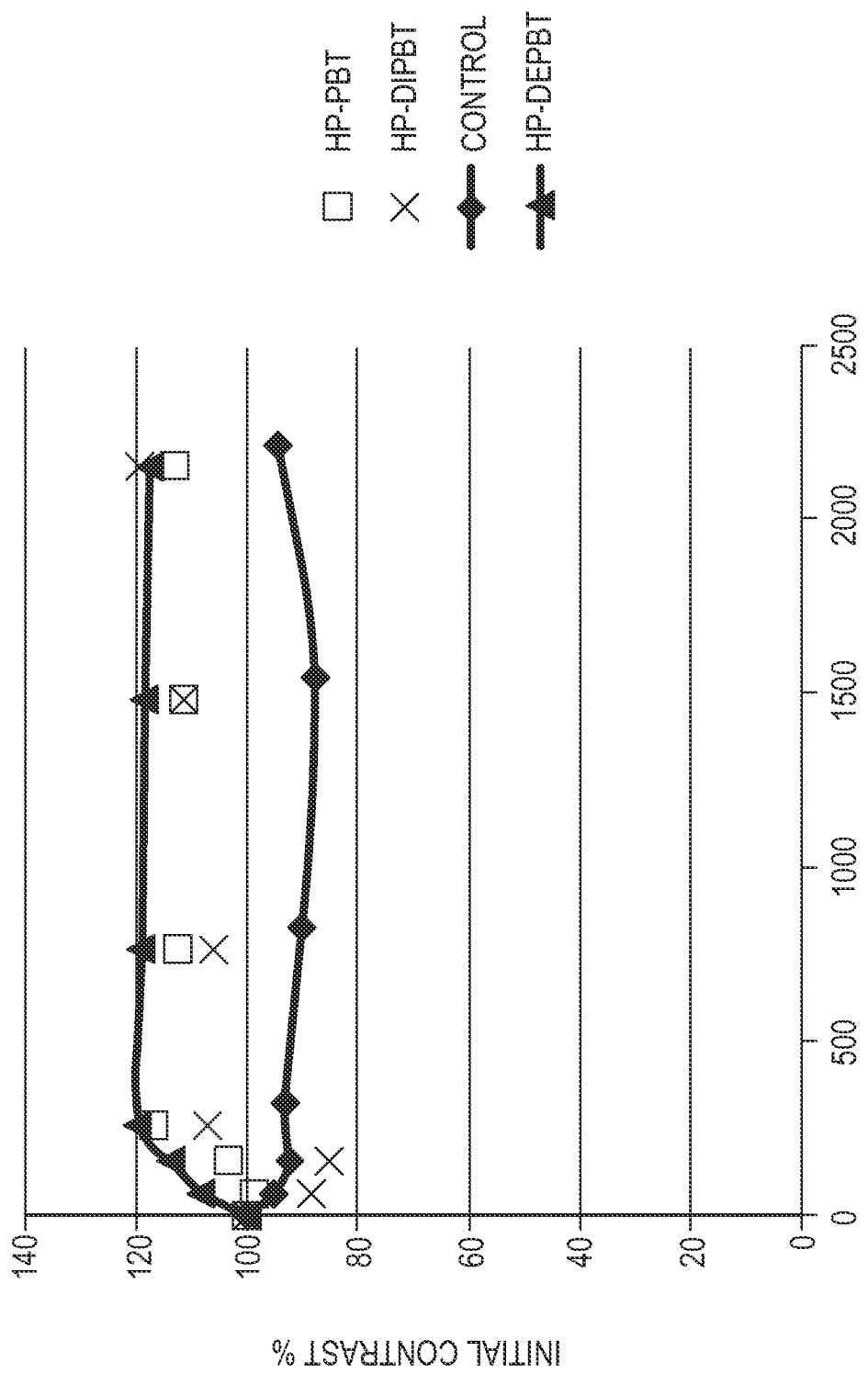
FIG. 6, on coordinates of initial contrast (in %) and normalized test time, is a plot of the percent initial contrast as a function of test time, in accordance with an example.

FIG. 6 shows the percent initial contrast vs. normalized test time. The term "normalized test times" refers to how long an ink can be maintained in a given state, e.g., the light state. The device containing the new surfactant had better initial contrast and retention of the initial contrast than the control.

In summary, the present disclosure is related to new surfactants and improved electronic inks based on these new surfactants with reduced conductivities and improved reliabilities. By replacing terminal primary amine groups on conventional surfactants with dialkyl-substituted or cycloalkyl-substituted tertiary amines, a series of new surfactants is obtained. These new surfactants have lower conductivities compared with conventional primary amine-based surfactants. Electronic inks based on these new surfactants have improved reliabilities.

What is claimed is:

1. A surfactant having a structure selected from the group consisting of:

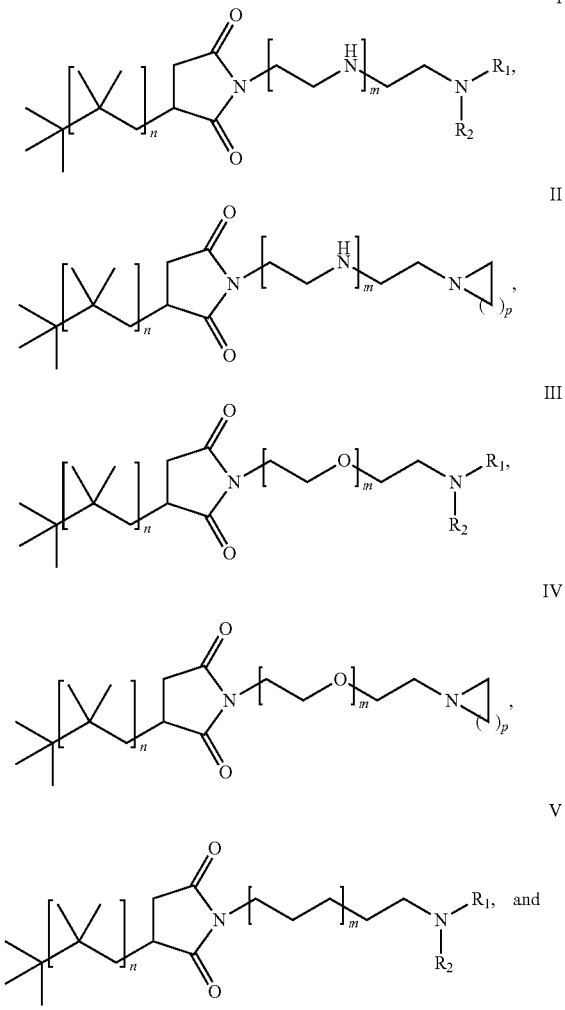

-continued

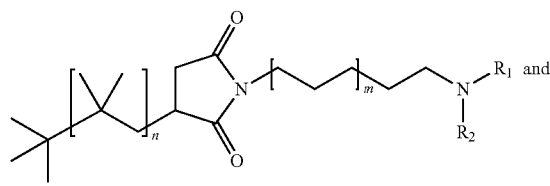

wherein
the letters $R_1$ to $R_2$ each independently represent an optionally substituted alkyl, alkenyl, aryl or aralkyl groups;
the letter m is an integer from 1 to 6 for structure I, and the letter m is an integer from 0 to 6 for structures II-VI;
the letter n is an integer from 5 to 500; and
the letter p is an integer from 1 to 6.

2. The surfactant of claim 1 wherein the surfactant is based on polyaliphatic amines and is selected from the group consisting of:

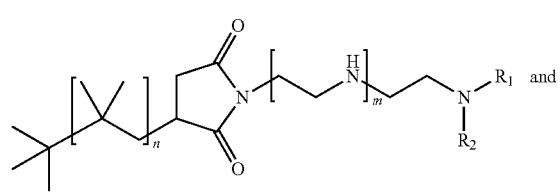

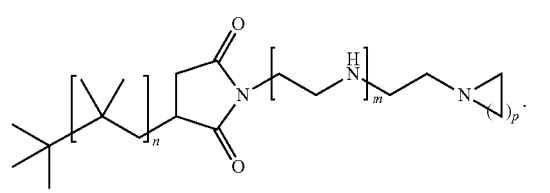

3. The surfactant of claim 1 wherein the surfactant is based on tertiary amine-terminated polyethylene glycols and is selected from the group consisting of

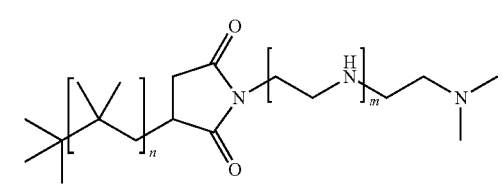

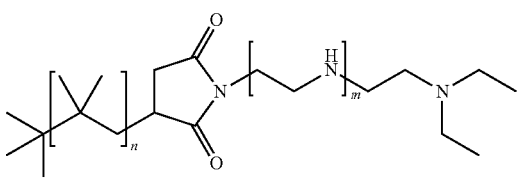

4. The surfactant of claim 1 wherein the surfactant is based on tertiary amine-terminated alkanes and is selected from the group consisting of:

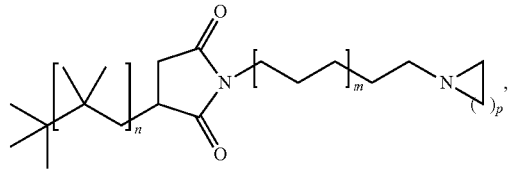

5. A surfactant having a structure selected from the group consisting of:

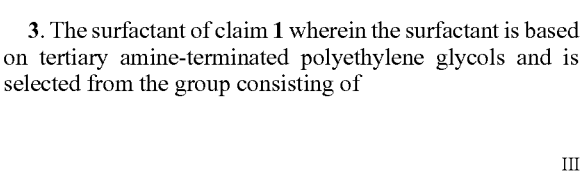

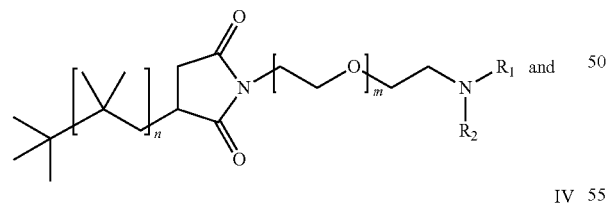

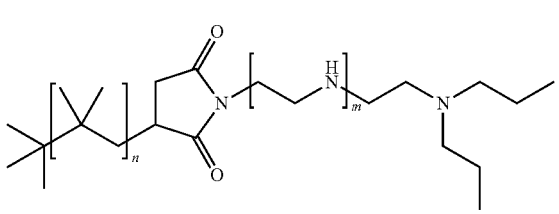

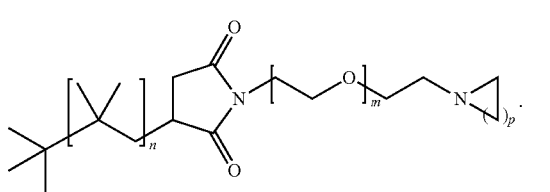

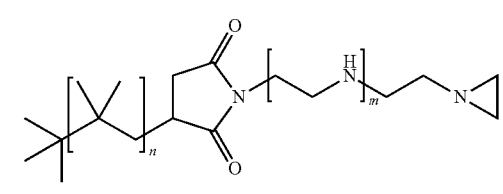

6
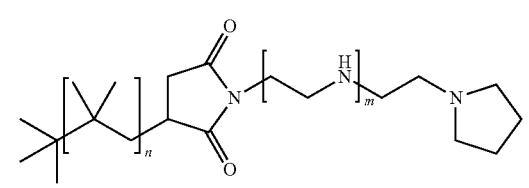
7
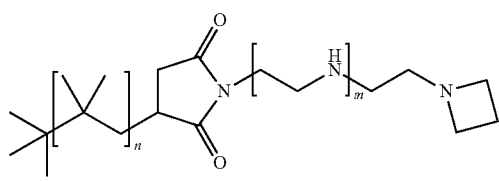
8
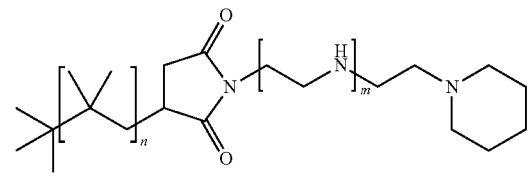
9
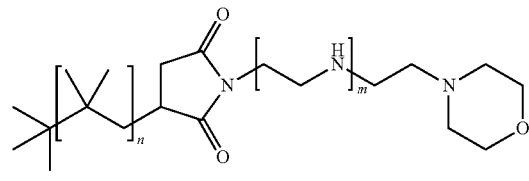
10
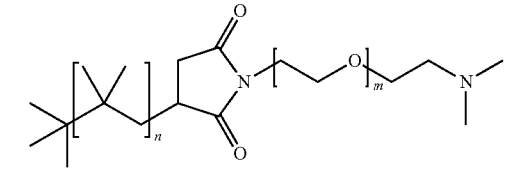
11
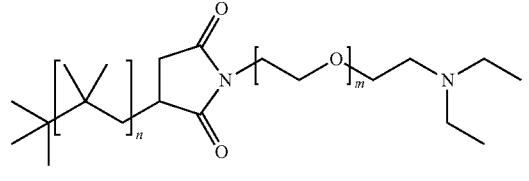
12
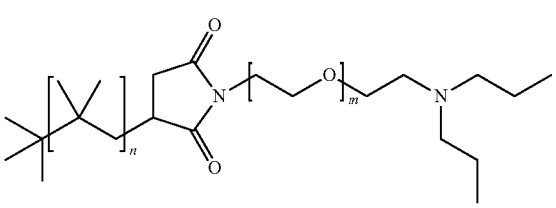
13
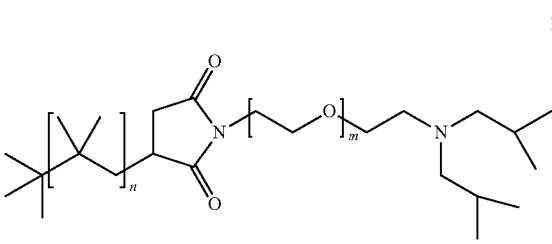
14
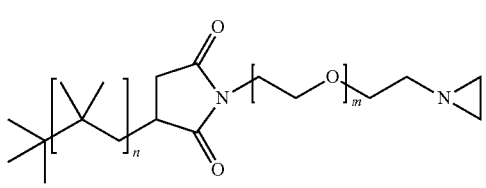
15
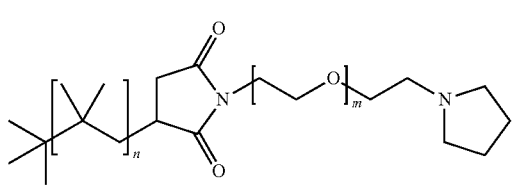
16
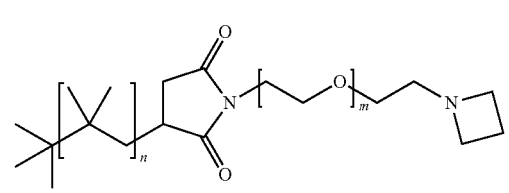
17
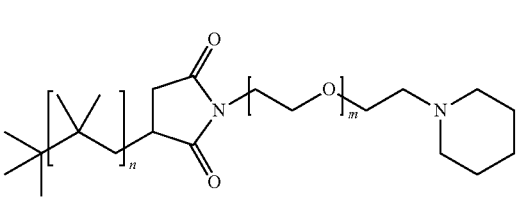
18
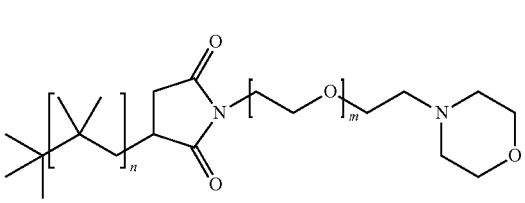
19
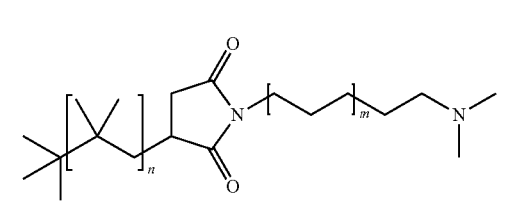
20
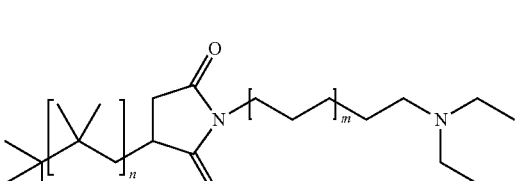
21
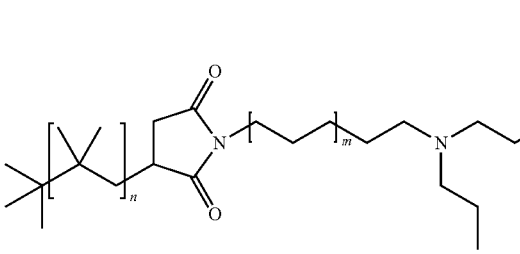

wherein
- the letter m is an integer from 1 to 6 for structures 1-4, and the letter m is an integer from 0 to 6 for structures 5-27; and
- the letter n is an integer from 5 to 500.

6. Pigment-based inks including:
- a non-polar carrier fluid;
- a pigment; and
- the surfactant of claim 1.

7. The inks of claim 6 wherein the non-polar carrier fluid is a non-polar solvent selected from the group consisting of hydrocarbons, halogenated hydrocarbons, partially halogenated hydrocarbons, and siloxanes.

8. The inks of claim 6 wherein the pigment is selected from the group consisting of black pigments, yellow pigments, magenta pigments, red pigments, violet pigments, cyan pigments, blue pigments, green pigments, orange pigments, brown pigments, and white pigments.

9. In combination, an electronic display and an electronic ink, wherein the electronic display includes:
- a first electrode;
- a second electrode; and
- a display cell having a recess defined by a dielectric material, the first electrode, and the second electrode, the display cell containing the electronic ink; and wherein the electronic ink includes:
  - a non-polar carrier fluid;
  - a pigment; and
  - the surfactant of claim 1.

10. The combination of claim 9 wherein the electronic display includes a plurality of display cells in a stacked configuration, associated first electrodes and second electrodes, and a plurality of electronic inks of different colors, each display cell containing an electronic ink of a different color.

11. The combination of claim 9 wherein the non-polar carrier fluid is a non-polar solvent selected from the group consisting of hydrocarbons, halogenated hydrocarbons, partially halogenated hydrocarbons, and siloxanes.

12. The combination of claim 10 wherein the colored pigment is a colored polymeric particle having a size ranging from 1 nm to 10 μm and is selected from the group consisting of black pigment particles, yellow pigment particles, magenta pigment particles, red pigment particles, violet pigment particles, cyan pigment particles, blue pigment particles, green pigment particles, orange pigment particles, brown pigment particles, and white pigment particles.

13. The combination of claim 9 wherein the surfactants have a hydrophobic tail and a hydrophilic head and are selected from the group consisting of dialkyl-substituted and cycloalkyl-substituted polyaliphatic amines, dialkyl and cycloalkyl tertiary amine-terminated polyethylene glycols, and dialkyl and cycloalkyl tertiary amine-terminated alkanes, the surfactants having polyisobutylene chains as the hydrophobic tail and the polyaliphatic amines having dialkyl or cycloalkyl substituted polyaliphatic amines as the hydrophilic head, or the polyethylene glycol amines having dialkyl or cycloalkyl tertiary amine-terminated polyethylene glycols as the hydrophilic head, or the alkane amines having dialkyl or cycloalkyl tertiary amine-terminated alkanes as the hydrophilic head.

14. A method for reducing conductivity in primary amine-based surfactants and improving reliability of electronic inks employing such surfactants, the method comprising replacing a terminal primary amine group on the surfactants with a dialkyl-substituted tertiary amine or a cycloalkyl-substituted tertiary amine to result in a structure as in claim 1.

15. Pigment-based inks including:
- a non-polar carrier fluid;
- a pigment; and
- the surfactant of claim 5.

16. The inks of claim 15 wherein the non-polar carrier fluid is a non-polar solvent selected from the group consisting of hydrocarbons, halogenated hydrocarbons, partially halogenated hydrocarbons, and siloxanes.

17. The inks of claim 15 wherein the pigment is selected from the group consisting of black pigments, yellow pigments, magenta pigments, red pigments, violet pigments, cyan pigments, blue pigments, green pigments, orange pigments, brown pigments, and white pigments.

18. In combination, an electronic display and an electronic ink, wherein the electronic display includes:
- a first electrode;
- a second electrode; and a display cell having a recess defined by a dielectric material, the first electrode, and the second electrode, the display cell containing the electronic ink; and wherein the electronic ink includes:
a non-polar carrier fluid;
a pigment; and
the surfactant of claim 5.

19. The combination of claim 18 wherein the electronic display includes a plurality of display cells in a stacked configuration, associated first electrodes and second electrodes, and a plurality of electronic inks of different colors, each display cell containing an electronic ink of a different color.

20. The combination of claim 18 wherein the non-polar carrier fluid is a non-polar solvent selected from the group consisting of hydrocarbons, halogenated hydrocarbons, partially halogenated hydrocarbons, and siloxanes; and wherein the colored pigment is a colored polymeric particle having a size ranging from 1 nm to 10 μm and is selected from the group consisting of black pigment particles, yellow pigment particles, magenta pigment particles, red pigment particles, violet pigment particles, cyan pigment particles, blue pigment particles, green pigment particles, orange pigment particles, brown pigment particles, and white pigment particles.

* * * * *